United States Patent [19]

Stetter et al.

[11] 4,344,953
[45] Aug. 17, 1982

[54] COMBATING PESTS WITH SUBSTITUTED ALKANYLAZOLYL OXIME-CARBAMATES

[75] Inventors: Jörg Stetter, Wuppertal; Bernhard Homeyer, Leverkusen; Ingeborg Hammann, Cologne, all of Fed. Rep. of Germany

[73] Assignee: Bayer Aktiengesellschaft, Leverkusen, Fed. Rep. of Germany

[21] Appl. No.: 182,380

[22] Filed: Aug. 29, 1980

Related U.S. Application Data

[63] Continuation of Ser. No. 31,098, Apr. 18, 1979, abandoned.

[30] Foreign Application Priority Data

May 10, 1978 [DE] Fed. Rep. of Germany ....... 2820361

[51] Int. Cl.$^3$ .................... A01N 43/50; A01N 43/64; C07D 233/61; C07D 249/08
[52] U.S. Cl. .................................. 424/269; 424/232; 424/245; 424/273 R; 424/273 P; 424/273 B; 424/273 N; 548/101; 548/255; 548/261; 548/262; 548/330; 548/341; 548/371; 548/378; 564/254; 568/419
[58] Field of Search ...................... 548/101, 262, 341; 424/245, 269, 273 R

[56] References Cited

FOREIGN PATENT DOCUMENTS 2613167 11/1977 Fed. Rep. of Germany ...... 424/269
2635883 2/1978 Fed. Rep. of Germany ...... 424/269

OTHER PUBLICATIONS

Brown, Insect Control by Chemicals, (New York, 1951), pp. 81–84.

Primary Examiner—Alton D. Rollins
Attorney, Agent, or Firm—Sprung, Horn, Kramer & Woods

[57] ABSTRACT

Substituted alkanyl-azolyl oxime-carbamates of the formula

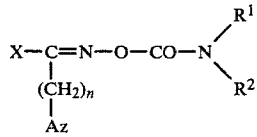

in which
Az represents an optionally substituted azolyl radical,
$R^1$ represents hydrogen or alkyl,
$R^2$ represents hydrogen, alkyl, alkenyl, alkynyl, halogenoalkyl, halogenoalkenyl or alkoxyalkyl, or, provided $R^1$ represents alkyl, $R^2$ may represent the $-(S)_m-R^3$ group,
$R^3$ represents alkyl, halogenoalkyl, optionally substituted phenyl, alkoxycarbonyl, the $-NR^4R^5$ group or a radical identical to that to which the $-(S)_n-R^3$ group is bonded,
$R^4$ represents alkyl,
$R^5$ represents alkyl, dialkylcarbamoyl, alkoxycarbonyl, alkenyloxycarbonyl, alkynyloxycarbonyl or optionally substituted phenylsulphonyl, or
$R^4$ and $R^5$, together with the N atom, represent a ring, which optionally contains a further heteroatom,
X represents substituted alkyl,
m represents 1 or 2 and
n represents 0 or 1, and physiologically acceptable acid addition salts and metal salt complexes thereof which possess arthropodicidal and nematocidal properties.

11 Claims, No Drawings

COMBATING PESTS WITH SUBSTITUTED ALKANYLAZOLYL OXIME-CARBAMATES

This is a continuation of application Ser. No. 31,098, filed Apr. 18, 1979 now abandoned.

The present invention relates to and has for its objects the provision of particular new substituted alkanyl-azolyl oxime-carbamates which possess arthropodicidal and nematocidal properties, active compositions in the form of mixtures of such compounds with solid and liquid dispersible carrier vehicles, and methods for producing such compounds and for using such compounds in a new way especially for combating pests, e.g. insects, acarids and nematodes, with other and further objects becoming apparent from a study of the within specification and accompanying examples.

It has already been disclosed that unsubstituted alkanyl-azolyl oxime-carbamates have good insecticidal, acaricidal and nematocidal properties (see DE-OS (German Published Specification) No. 2,613,167 and DE-OS (German Published Specification No. 2,635,883). However, their action is not always completely satisfactory, especially when low amounts are applied.

The present invention now provides, as new compounds, the substituted alkanyl-azolyl oxime-carbamates of the general formula

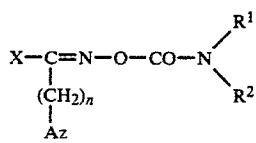

in which
Az represents an optionally substituted azolyl radical,
$R^1$ represents hydrogen or alkyl,
$R^2$ represents hydrogen, alkyl, alkenyl, alkynyl, halogenoalkyl, halogenoalkenyl or alkoxyalkyl, or, provided $R^1$ represents alkyl, $R^2$ may represent the $-(S)_m-R^3$ group,
$R^3$ represents alkyl, halogenoalkyl, optionally substituted phenyl, alkoxycarbonyl, the $-NR^4R^5$ group or a radical identical to that which the $-(S)_m-R^3$ group is bonded,
$R^4$ represents alkyl and
$R^5$ represents alkyl, dialkylcarbamoyl, alkoxycarbonyl, alkenyloxycarbonyl, alkynyloxycarbonyl or optionally substituted phenylsulphonyl, or
$R^4$ and $R^5$, together with the N atom, represent a ring, which optionally contains a further heteroatom,
X represents substituted alkyl,
m represents 1 or 2 and
n represents 0 or 1,
and physiologically acceptable acid addition salts and metal salt complexes thereof. They display powerful insecticidal, acaricidal and nematocidal properties.

Preferably, Az represents an optionally substituted pyrazol-1-yl, imidazol-1-yl, 1,2,4-triazol-1-yl, 1,2,3-triazol-1-yl, 1,3,4-triazol-1-yl, indazol-1-yl, benzimidazol-1-yl or benztriazol-1-yl radical, preferred substituents being halogen (especially fluorine, chlorine and bromine), alkyl with 1 to 4 carbon atoms, halogenoalkyl with up to 2 carbon atoms and up to 5 halogen atoms (especially fluorine and chlorine atoms, trifluoromethyl being mentioned as an example), alkoxy with up to 4 carbon atoms, alkylthio with up to 4 carbon atoms and nitro;

$R^1$ represents hydrogen or straight-chain or branched alkyl with 1 to 4 carbon atoms;

$R^2$ represents hydrogen, straight-chain or branched alkyl with 1 to 12 carbon atoms, alkenyl with 2 to 4 carbon atoms, alkynyl with 2 to 4 carbon atoms, halogenoalkyl with up to 2 carbon atoms and up to 5 halogen atoms (especially fluorine and chlorine atoms), halogenoalkenyl with 2 to 4 carbon atoms and up to 5 halogen atoms (especially fluorine and chlorine atoms) or alkoxyalkyl with up to 2 carbon atoms in each alkyl part or, provided $R^1$ represents alkyl, $R^2$ may represent the $-(S)_m-R^3$ group;

$R^3$ is straight-chain or branched alkyl with 1 to 4 carbon atoms, halogenoalkyl with 1 to 2 carbon atoms and up to 5 halogen atoms (especially fluorine and chlorine atoms, trifluoromethyl being mentioned as an example), optionally substituted phenyl [preferred substituents being halogen (especially fluorine, chlorine or bromine), alkyl with 1 or 2 carbon atoms and halogenoalkyl with 1 to 2 carbon atoms and up to 5 halogen atoms (especially fluorine and chlorine atoms, the trifluoromethyl group being mentioned as an example)] or alkoxycarbonyl with 1 to 4 carbon atoms in the alkoxy part, or $R^3$ represents a radical identical to that to which the $-(S)_m-R^3$ group is bonded or represents the $-NR^4R^5$ group;

$R^4$ represents straight-chain or branched alkyl with 1 to 4 carbon atoms and $R^5$ represents straight-chain or branched alkyl with 1 to 4 carbon atoms, dialkylcarbamoyl with 1 to 4 carbon atoms in each alkyl part, alkoxycarbonyl with 1 to 4 carbon atoms in the alkyl part, alkenyloxycarbonyl with 2 to 4 carbon atoms in the alkenyl part, alkynyloxycarbonyl with 2 to 4 carbon atoms in the alkynyl part or optionally substituted phenylsulphonyl, preferred substituents being halogen (especially fluorine, chlorine or bromine), alkyl with 1 to 2 carbon atoms and halogenoalkyl with 1 to 2 carbon atoms and up to 5 halogen atoms (especially fluorine and chlorine atoms, trifluoromethyl being mentioned as an example) or $R^4$ and $R^5$, together with the nitrogen atom, represent a five-membered to seven-membered ring, which can optionally contain nitrogen and/or oxygen as further heteroatoms; and X represents monosubstituted or disubstituted alkyl with 1 to 4 carbon atoms, preferred substituents being halogen (especially fluorine, chlorine or bromine), acyloxy (especially alkylcarbonyloxy with 1 to 4 carbon atoms in the alkyl part), carbamoyloxy, alkylcarbamoyloxy and dialkylcarbamoyloxy with in either case 1 to 4 carbon atoms per alkyl part, alkylsulphonyloxy with 1 to 4 carbon atoms, hydroxyl, nitro, cyano, alkoxycarbonyl with 1 to 4 carbon atoms in the alkyl part and alkoxy and alkylthio with in either case 1 to 4 carbon atoms, it being possible for the alkyl groups of two alkoxy or alkylthio substituents to be linked to one another in the form of a 5-membered or 6-membered ring.

The compounds of the formula (I) can exist in the syn form or the anti form; they are predominantly obtained as mixtures of the two forms.

The invention also provides a process for the preparation of a substituted alkanyl-azolyl oxime-carbamate of the general formula (I) in which
(a) an oxime of the general formula

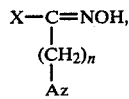 (II)

in which

Az, X and n have the meanings stated above, is reacted with a carbamoyl halide of the general formula

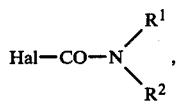 (III)

in which

R¹ and R² have the meanings stated above and

Hal represents fluorine or chlorine, either in the presence of a diluent and an acid-binding agent or in the presence of a diluent and sodium hydride, or (b) an oxime of the formula (II) is reacted with an isocyanate of the general formula

 (IV), in which

R represents alkyl, alkenyl, alkynyl, halogenoalkyl, halogenoalkenyl or alkoxyalkyl, in the presence of a diluent and if appropriate in the presence of a catalyst, or (c) an oxime of the formula (II) is reacted with phosgene and the product is then reacted with an amine of the general formula

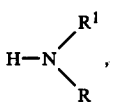 (V)

in which

R and R¹ have the meanings stated above but

R may alternatively represent hydrogen, either in the presence of a diluent and an acid-binding agent or in the presence of a diluent and sodium hydride, or (d) an oxime-carbamate obtainable by process variant (a), (b) or (c), of the general formula

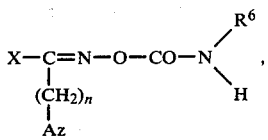 (VI)

in which

Az, X and n have the meanings stated above and

R⁶ represents alkyl with 1 to 4 carbon atoms, is reacted with a sulphenyl chloride of the general formula

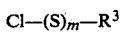 (VII), in which

R³ and m have the meanings stated above, in the presence of a diluent and an acid-binding agent.

Furthermore, the substituted alkanyl-azolyl oxime-carbamates of the formula (I) obtainable according to the invention can be converted into salts by reaction with acids, and the corresponding metal complexes can be obtained by reaction with metal salts.

Surprisingly, the substituted alkanyl-azolyl oxime-carbamates according to the invention exhibit a higher insecticidal, acaricidal and nematocidal action than the known unsubstituted alkanyl-azolyl oxime-carbamates, which are very closely related compounds chemically and from the point of view of their action. The active compounds according to the invention thus represent an enrichment of the art.

The particularly preferred substituted alkanyl-azolyl oxime-carbamates of the formula (I) are those in which Az represents a pyrazol-1-yl, imidazol-1-yl, 1,2,4-triazol-1-yl, 1,2,3-triazol-1-yl or 1,3,4-triazol-1-yl radical which is optionally substituted by chlorine, methyl, ethyl, nitro or methylmercapto; R¹ represents hydrogen or methyl; R² represents methyl, methoxymethyl, allyl or the—(S)$_m$—R³ group; if m represents 1, R³ represents methoxycarbonyl, trichloromethyl, dichlorofluoromethyl, phenyl which is optionally substituted by chlorine or trifluoromethyl or the —NR⁴R⁵ group; or, if m represents 1 or 2, R³ denotes a radical identical to that to which the —(S)$_m$—R³ group is bonded; R⁴ represents methyl and R⁵ represents methyl, methoxycarbonyl or methylphenylsulphonyl; or R⁴ and R⁵ together represent piperidinyl or morpholino; X represents tertiary butyl which is optionally monosubstituted or disubstituted, the substituents being selected from chlorine, fluorine, bromine, hydroxyl, acetoxy, methylcarbamoyloxy and dimethylcarbamoyloxy; and n represents 0 or 1.

Specific compounds which may be mentioned, in addition to those given in the preparative examples are the following:

TABLE 1

$$X-\underset{\underset{\underset{Az}{|}}{(CH_2)_n}}{C}=N-O-CO-N\underset{R^2}{\overset{R^1}{\diagup}} \quad (I)$$

| X | Az | n | R¹ | R² |
|---|---|---|---|---|
| ClCH$_2$-C(CH$_3$)$_2$- | 1,2,4-triazol-1-yl (N=CH-N=CH-N-) | 1 | H | -S-C$_6$H$_4$-Cl |
| ClCH$_2$-C(CH$_3$)$_2$- | 1,2,4-triazol-1-yl | 1 | H | dimer |
| ClCH$_2$-C(CH$_3$)$_2$- | imidazol-1-yl | 1 | H | CH$_3$ |
| ClCH$_2$-C(CH$_3$)$_2$- | 5-nitroimidazol-1-yl | 1 | H | CH$_3$ |
| ClCH$_2$-C(CH$_3$)$_2$- | 2-methyl-5-nitroimidazol-1-yl (with CH$_3$) | 1 | H | CH$_3$ |
| ClCH$_2$-C(CH$_3$)$_2$- | 2-methyl-5-nitroimidazol-1-yl | 1 | H | CH$_3$ |
| FCH$_2$-C(CH$_3$)$_2$- | 4-nitroimidazol-1-yl | 1 | H | CH$_3$ |
| FCH$_2$-C(CH$_3$)$_2$- | pyrazol-1-yl | 1 | H | CH$_3$ |
| FCH$_2$-C(CH$_3$)$_2$- | imidazol-1-yl | 1 | H | CH$_3$ |
| FCH$_2$-C(CH$_3$)$_2$- | 4-nitropyrazol-1-yl | 1 | H | CH$_3$ |

TABLE 1-continued $$X-C=N-O-CO-N\begin{matrix}R^1\\R^2\end{matrix} \quad (I)$$
$$\underset{Az}{|}(CH_2)_n$$

| X | Az | n | R¹ | R² |
|---|---|---|---|---|
| FCH₂-C(CH₃)₂- | 5-O₂N, 4-CH₃, 1-CH₃-imidazole (N-linked at 2?) | 1 | H | CH₃ |
| CH₃S-C(CH₃)₂- | 1-methyl-1,2,4-triazol-3-yl | 1 | H | CH₃ |
| CH₃O-C(CH₃)₂- | 1-methyl-1,2,4-triazol-3-yl | 1 | H | CH₃ |
| NC-C(CH₃)₂- | 1-methyl-1,2,4-triazol-3-yl | 1 | H | CH₃ |
| FCH₂-C(CH₃)₂- | 1-methyl-1,2,4-triazol-3-yl | 1 | H | CH₃ |
| ClCH₂-C(CH₃)₂- | 1-methyl-1,2,4-triazol-3-yl | 1 | H | CH₃ |
| CH₃S-CH₂-C(CH₃)₂- | 1-methyl-1,2,4-triazol-3-yl | 1 | H | CH₃ |
| CH₃O-CH₂-C(CH₃)₂- | 1-methyl-1,2,4-triazol-3-yl | 1 | H | CH₃ |
| H₅C₂O₂C-C(CH₃)₂- | 1-methyl-1,2,4-triazol-3-yl | 1 | H | CH₃ |
| H₅C₂O₂C-H₂C-C(CH₃)₂- | 1-methyl-1,2,4-triazol-3-yl | 1 | H | CH₃ |

TABLE 1-continued $$X-C=N-O-CO-N\begin{matrix}R^1\\R^2\end{matrix} \quad (I)$$
$$\underset{Az}{|}(CH_2)_n$$

| X | Az | n | R¹ | R² |
|---|---|---|---|---|
| F-CH₂-C(CH₃)₂- | 1,2,4-triazol-1-yl | 0 | H | CH₃ |
| F-CH₂-C(CH₃)₂- | pyrazol-1-yl | 0 | H | CH₃ |
| F-CH₂-C(CH₃)₂- | 1,2,4-triazol-1-yl | 0 | H | dimer |
| Cl-CH₂-C(CH₃)₂- | 1,2,4-triazol-1-yl | 0 | H | -S-C₆H₄-Cl |
| ClCH₂-C(CH₃)₂- | pyrazol-1-yl | 0 | H | CH₃ |
| ClCH₂-C(CH₃)₂- | pyrazol-1-yl | 0 | H | -S-C₆H₄-Cl |
| CH₃O-CH₂-C(CH₃)₂- | 1,2,4-triazol-1-yl | 0 | H | CH₃ |
| CH₃S-CH₂-C(CH₃)₂- | 1,2,4-triazol-1-yl | 0 | H | CH₃ |
| NC-CH₂-CH₂-C(CH₃)₂- | 1,2,4-triazol-1-yl | 0 | H | CH₃ |
| CH₃S-C(CH₃)₂- | 1,2,4-triazol-1-yl | 0 | H | CH₃ |

TABLE 1-continued $$X-\underset{\underset{Az}{|}}{\underset{(CH_2)_n}{C}}=N-O-CO-N\underset{R^2}{\overset{R^1}{\diagdown}} \quad (I)$$

| X | Az | n | R¹ | R² |
|---|---|---|---|---|
| $CH_3O-\underset{CH_3}{\overset{CH_3}{\underset{|}{\overset{|}{C}}}}-$ | 1,2,4-triazol-1-yl | 0 | H | $CH_3$ |
| $NC-\underset{CH_3}{\overset{CH_3}{\underset{|}{\overset{|}{C}}}}-$ | 1,2,4-triazol-1-yl | 0 | H | $CH_3$ |
| $BrCH_2-\underset{CH_3}{\overset{CH_3}{\underset{|}{\overset{|}{C}}}}-$ | 1,2,4-triazol-1-yl | 0 | H | $CH_3$ |
| $CH_3-CO-O-\underset{CH_3}{\overset{CH_3}{\underset{|}{\overset{|}{C}}}}-$ | 1,2,4-triazol-1-yl | 0 | H | $CH_3$ |

If, for example, 4-chloro-3,3-dimethyl-2-oximino-1-(1,2,4-triazol-1-yl)-butane and dimethylcarbamoyl chloride are used as starting substances in process variant (a), the course of the reaction can be represented by the equation which follows:

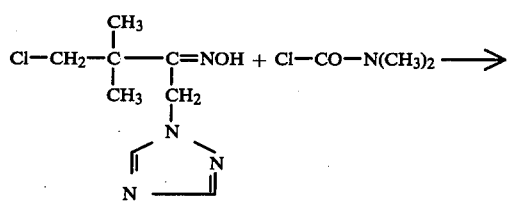

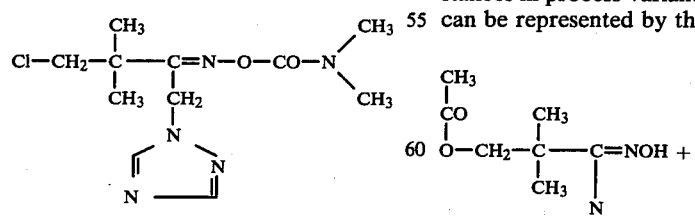

If, for example, 4-chloro-3,3-dimethyl-2-oximino-1-(pyrazol-1-yl)-butane and N-methyl-N-trichloromethyl-mercapto-carbamoyl fluoride are used as starting substances in process variant (a), the course of the reaction can be represented by the equation which follows:

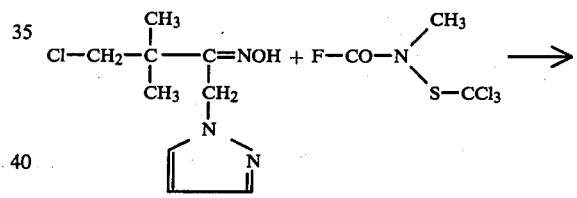

If, for example, 3-acetoxy-2,2-dimethyl-1-oximino-1(1,2,4-triazol-1-yl)-propane and N,N'-bis-(fluorocarbonyl)thio-bis-methylamine are used as starting substances in process variant (a), the course of the reaction can be represented by the equation which follows:

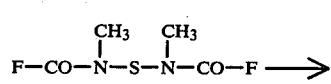

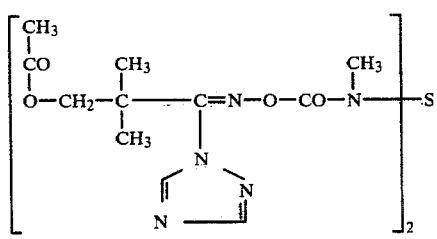

If 3,3-dimethyl-4-hydroxy-2-oximino-1-(1,2,4-triazol-1-yl)-butane and methyl isocyanate are used as starting substances in process variant (b), the course of the reaction can be represented by the equation which follows:

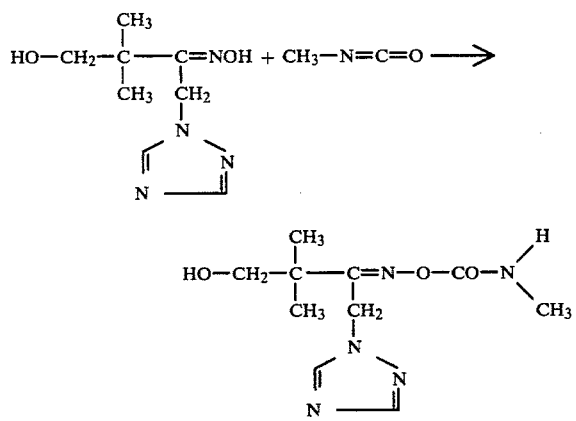

If 4-chloro-3,3-dimethyl-1-(imidazol-1-yl)-2-oximino butane, phosgene and dimethylamine are used as starting substances in process variant (c), the course of the reaction can be represented by the equation which follows:

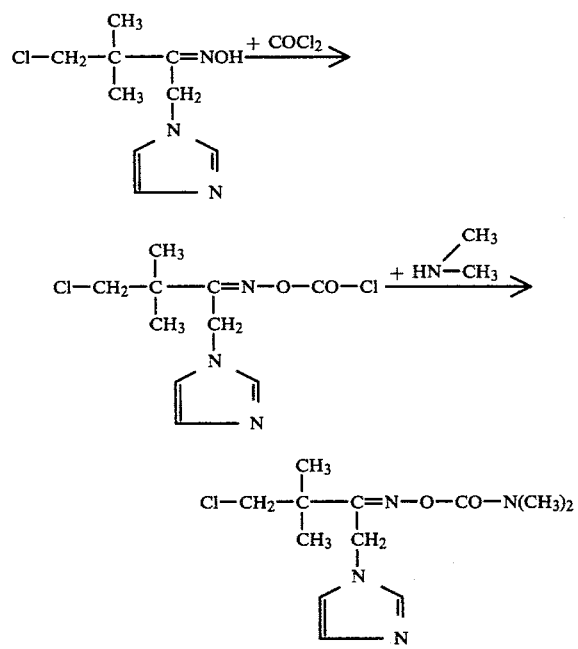

If 2,2-dimethyl-3-fluoro-1-methylcarbamoyloximino-1-(pyrazol-1-yl)-propane and 4-chlorophenyl-sulphenyl chloride are used as starting substances in process variant (d), the course of the reaction can be represented by the equation which follows:

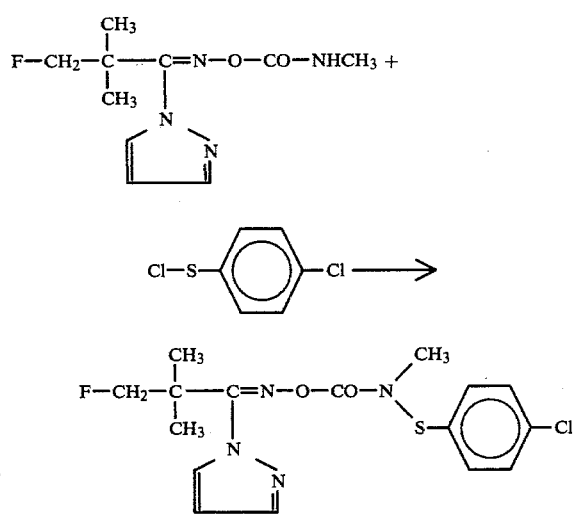

The oximes of the formula (II) can be obtained as described in U.S. Ser. No. 819,021.

The oximes of the formula (II) in which n represents 0 can be prepared by reacting hydroxamic acid halides of the general formula

(VIII)

in which
X has the meaning stated above and
Y represents halogen, especially chlorine or bromine, with azoles of the general formula

(IX), in which
Az has the meaning stated above, in the presence of an organic solvent, for example tetrahydrofuran, and in the presence of an acid-binding agent, for example trimethylamine or excess azole, at a temperature between 0° and 80° C., preferably between 0° and 40° C. Isolation of the compounds of the formula (II) is effected by adding water to the reaction mixture, filtering off and drying the precipitate formed and purifying it, if appropriate, by recrystallization.

The hydroxamic acid halides of the formula (VIII) used as starting substances are known (see H. Ulrich "The Chemistry of Imidoyl Halides," pages 157–172, Plenum Press, New York 1968 and the literature references quoted therein). Those which are not yet known can easily be prepared by the processes described in the literature, for example by chlorinating the corresponding aldoximes.

The oximes of the formula (II) in which n represents 1 can be prepared by reacting azolyl ketones of the general formula

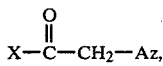

in which

Az and X have the meanings stated above, with hydroxylamine in the presence of a solvent, preferably alcohols or aqueous alcohols, at temperatures between 20° and 100° C., preferably between 50° and 80° C. The hydroxylamine is preferably employed in the form of its salts, in particular as the hydrochloride, in the presence of an acid-binding agent, for example sodium carbonate. Isolation of the compounds of the formula (II) is effected by working up, by customary methods, the product formed during the reaction, after distilling off the solvent.

The azolyl ketones of the formula (X) can be obtained by reacting halogenoketones of the formula

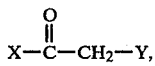

in which

X has the meaning stated above and

Y represents chlorine or bromine, with azoles of the formula (IX) in the presence of a diluent, for example methyl ethyl ketone, and in the presence of an acid-binding agent, for example potassium carbonate, at temperatures between 20° and 150° C., preferably between 60° and 120° C. Isolation of the compounds of the formula (XI) is effected by filtering off the salt formed during the reaction and concentrating the filtrate by distilling off the solvent. The solid which thereby remains is dried and purified by recrystallization.

Examples which may be mentioned of starting substances of the formula (II) are: 4-chloro-3,3-dimethyl-2-oximino-1-(1,2,4-triazol-1-yl)-butane, 4-chloro-3,3-dimethyl-2-oximino-1-(pyrazol-1-yl)-butane, 4-chloro-3,3-dimethyl-2-oximino-1-(imidazol-1-yl)-butane, 4-chloro-3,3-dimethyl-2-oximino-1-(5-methyl-4-nitro-imidazol-1-yl)-butane, 4-chloro-3,3-dimethyl-2-oximino-1-(4-nitro-imidazol-1-yl)-butane, 4-chloro-3,3-dimethyl-2-oximino-1-(2-methyl-4-nitro-imidazol-1-yl)-butane, 4-methylthio-3,3-dimethyl-2-oximino-1-(1,2,4-triazol-1-yl)-butane, 4-methylthio-3,3-dimethyl-2-oximino-1-(pyrazol-1-yl)-butane, 4-methylthio-3,3-dimethyl-2-oximino-1-(imidazol-1-yl)-butane, 4-methylthio-3,3-dimethyl-2-oximino-1-(5-methyl-4-nitro-imidazolyl-1-yl)-butane, 4-methylthio-3,3-dimethyl-2-oximino-1-(4-nitro-imidazol-1-yl)-butane, 4-methylthio-3,3-dimethyl-2-oximino-1-(2-methyl-4-nitro-imidazol-1-yl)-butane, 4-fluoro-3,3-dimethyl-2-oximino-1-(1,2,4-triazol-1-yl)-butane, 4-fluoro-3,3-dimethyl-2-oximino-1-(pyrazol-1-yl)-butane, 4-fluoro-3,3-dimethyl-2-oximino-1-(imidazol-1-yl)-butane, 4-fluoro-3,3-dimethyl-2-oximino-1-(5-methyl-4-nitro-imidazol-1-yl)-butane, 4-fluoro-3,3-dimethyl-2-oximino-1-(4-nitro-imidazol-1-yl)-butane, 4-fluoro-3,3-dimethyl-2-oximino-1-(2-methyl-4-nitro-imidazol-1-yl)-butane, 4-methoxy-3,3-dimethyl-2-oximino-1-(1,2,4-triazol-1-yl)-butane, 4-methoxy-3,3-dimethyl-2-oximino-1-(pyrazol-1-yl)-butane, 4-methoxy-3,3-dimethyl-2-oximino-1-(imidazol-1-yl)-butane, 4-methoxy-3,3-dimethyl-2-oximino-1-(5-methyl-4-nitro-imidazol-1-yl)-butane, 4-methoxy-3,3-dimethyl-2-oximino-1-(4-nitro-imidazol-1-yl)-butane, 4-methoxy-3,3-dimethyl-2-oximino-1-(2-methyl-4-nitro-imidazol-1-yl)-butane, 2-methyl-2-methoxy-1-oximino-1-(1,2,4-triazol-1-yl)-propane, 2-methyl-2-methoxy-1-oximino-1-(pyrazol-1-yl)-propane, 2-methyl-2-methoxy-1-oximino-1-(imidazol-1-yl)-propane, 2-methyl-2-methylthio-1-oximino-1-(1,2,4-triazol-1-yl)-propane, 2-methyl-2-methylthio-1-oximino-1-(pyrazol-1-yl)-propane, 2-methyl-2-methylthio-1-oximino-1-(imidazol-1-yl)-propane, 2-methyl-2-acetoxy-1-oximino-1-(1,2,4-triazol-1-yl)-propane, 2-methyl-2-acetoxy-1-oximino-1-(pyrazol-1-yl)-propane, 2-methyl-2-acetoxy-1-oximino-1-(imidazol-1-yl)-propane, 2-methyl-2-cyano-1-oximino-1-(1,2,4-triazol-1-yl)-propane, 2-methyl-2-cyano-1-oximino-1-(pyrazol-1-yl)-propane, 2-methyl-2-cyano-1-oximino-1-(imidazol-1-yl)-propane, 3-chloro-2,2-dimethyl-1-oximino-1-(1,2,4-triazol-1-yl)-propane, 3-chloro-2,2-dimethyl-1-oximino-1-(pyrazol-1-yl)-propane, 3-chloro-2,2-dimethyl-1-oximino-1-(imidazol-1-yl)-propane, 3-fluoro-2,2-dimethyl-1-oximino-1-(1,2,4-triazol-1-yl)-propane, 3-fluoro-2,2-dimethyl-1-oximino-1-(pyrazol-1-yl)-propane, 3-fluoro-2,2-dimethyl-1-oximino-1-(imidazol-1-yl)-propane, 3-methylthio-2,2-dimethyl-1-oximino-1-(1,2,4-triazol-1-yl)-propane, 3-methylthio-2,2-dimethyl-1-oximino-1-(pyrazol-1-yl)-propane, 3-methylthio-2,2-dimethyl-1-oximino-1-(imidazol-1-yl)-propane, 3-methoxy-2,2-dimethyl-1-oximino-1-(1,2,4-triazol-1-yl)-propane, 3-methoxy-2,2-dimethyl-1-oximino-1-(pyrazol-1-yl)-propane and 3-methoxy-2,2-dimethyl-1-oximino-1-(imidazol-1-yl)-propane.

Carbamoyl halides of the formula (III) are known and can be prepared by processes which are generally customary and known, for example they are obtained by reacting amines with phosgene (these processes are known from general textbooks of organic chemistry) or by reacting the corresponding carbamic acid halides with appropriate sulphenyl chlorides (in this context, see also the statements in DE-AS (German Published Specification) No. 1,297,095, DE-OS (German Published Specifications) No. 2,357,930 and 2,409,463, and U.S. Pat. No. 3,939,192).

Examples which may be mentioned of starting substances of the formula (III) are: dimethylcarbamoyl chloride, methylethylcarbamoyl chloride, allylmethylcarbamoyl chloride, methoxymethyl-methylcarbamoyl chloride, methyltrifluoromethylcarbamoyl chloride, ethylvinylcarbamoyl chloride, N-fluorodichloromethylsulphenyl-N-phenyl-carbamic acid fluoride, N,N'-bis-(fluorocarbonyl)-thio-bis-methylamine, N-methyl-N-trichloromethylsulphenyl-carbamic acid fluoride, N-methyl-N-fluorodichloromethylsulphenyl-carbamic acid fluoride, N-methyl-N-chlorodifluoromethylsulphenyl-carbamic acid fluoride, N-methyl-N-(3-trifloromethylphenyl)-sulphenyl-carbamic acid fluoride, N-methyl-N-(methoxycarbonyl-sulphenyl)-carbamic acid fluoride, N-methyl-N-[(3-methylphenyl-sulphonyl)-methylamino-sulphenyl)]-carbamic acid fluoride, N-methyl-N-[(4-chlorophenyl)-sulphenyl]-carbamic acid fluoride, N-methyl-N-[(4-methylphenyl-sulphonyl)-methylamino-sulphenyl]-carbamic acid fluoride and N-methyl-N-(morpholin-1-yl-sulphenyl)-carbamic acid fluoride, and the corresponding carbamic acid chlorides.

The formula (IV) provides a general definition of the isocyanates also required as starting substances for process variant (b) according to the invention. In this formula, R preferably represents straight-chain or branched alkyl with 1 to 12 carbon atoms, alkenyl or alkynyl with in either case 2 to 4 carbon atoms, halogenoalkyl with up to 2 carbon atoms and up to 5 halogen atoms (especially fluorine and chlorine atoms, trifluoromethyl being mentioned as an example), halogenoalkenyl with up to 3 carbon atoms and up to 5 halogen atoms (especially fluorine and chlorine atoms) or alkoxyalkyl with up to 2 carbon atoms in each alkyl part.

Isocyanates of the formula (IV) are known and can be prepared by processes which are generally customary and known, for example by reacting amines with phosgene and then heating the products. These processes are known from general textbooks of organic chemistry.

Examples which may be mentioned of starting substances of the formula (IV) are: chloroethyl isocyanate, trichlorovinyl isocyanate, methoxymethyl isocyanate, ethoxymethyl isocyanate, methoxyethyl isocyanate, cyclohexyl isocyanate, methyl isocyanate, ethyl isocyanate, i-propyl isocyanate, t.-butyl isocyanate, heptyl isocyanate, dodecyl isocyanate, allyl isocyanate, propargyl isocyanate, trifluoromethyl isocyanate and chloromethyl isocyanate.

The formula (V) provides a general definition of the amines also to be used as starting substances for process variant (c) according to the invention. In this formula, R preferably represents hydrogen or one of the radicals which have already been mentioned as preferred in the case of the isocyanates of the formula (IV).

The amines of the formula (V) are generally known compounds. Examples which may be mentioned are ammonia, methylamine, ethylamine, dimethylamine, methylethylamine, allylmethylamine, methoxymethyl-methylamine, methyl-trifluoromethylamine and ethylvinylamine.

The sulphenyl chlorides of the formula (VII) are generally known compounds of organic chemistry. Examples which may be mentioned are: trichloromethylsulphenyl chloride, dichlorofluoromethylsulphenyl chloride, chlorodifluoromethylsulphenyl chloride, trifluoromethylsulphenyl chloride, phenylsulphenyl chloride, 2,4-dichlorophenylsulphenyl chloride, 3-trifluoromethylsulphenyl chloride, 3-methylphenylsulphenyl chloride, methylsulphenyl chloride, 4-chloro-3-trifluoro-methylphenylsulphenyl chloride, methoxycarbonylsulphenyl chloride and ethoxycarbonylsulphenyl chloride.

All the physiologically acceptable acids can be used for the preparation of acid addition salts of the compounds of the formula (I). Preferred acids include hydrogen halide acids (for example hydrobromic acid and, especially, hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicylic acid, sorbic acid and lactic acid) and sulphonic acids (for example p-toluenesulphonic acid and 1,5-naphthalenedisulphonic acid).

The salts of the compounds of the formula (I) can be obtained in a simple manner by customary salt formation methods, for example by dissolving a compound of the formula (I) in a suitable inert solvent and adding the acid, for example hydrochloric acid, and can be isolated in a known manner, for example by filtration, and if appropriate purified by washing with an inert organic solvent.

Salts of metals of main groups II to IV and of subgroups I and II and IV to VIII of the Periodic Table can be used for the preparation of metal salt complexes of the compounds of the formula (I). examples of suitable metals being copper, zinc, manganese, magnesium, tin, iron and nickel. Possible anions of the salts are those which are derived from physiological acids, amongst which hydrogen halide acids (for example hydrochloric acid and hydrobromic acid), phosphoric acid, nitric acid and sulphuric acid are preferred. The metal salt complexes of the compounds of the formula (I) can be obtained in a simple manner by customary processes, for example by dissolving the metal salt in an alcohol, for example ethanol, and adding the solution to the compound of the formula (I). The metal salt complexes can be isolated in a known manner, for example by filtration, and if appropriate purified by recrystallization.

Preferred diluents for the reaction according to process variants (a), (b), (c) and (d) are all the inert organic solvents, especially ketones, such as diethyl ketone, and in particular acetone and methyl ethyl ketone; nitriles, such as propionitrile, and in particular acetonitrile; alcohols, such as ethanol or isopropanol; ethers, such as tetrahydrofuran or dioxane; formamides, such as, in particular, dimethylformamide; and halogenated hydrocarbons, such as methylene chloride, carbon tetrachloride or chloroform. When sodium hydride is used as an auxiliary, polar organic solvents, especially hexamethylphosphoric acid triamide, are preferably used.

If the reaction of processes (a), (c) and (d) is carried out in the presence of an acid-binding agent, it is possible to add any of the inorganic and organic acid-binding agents which can customarily be used. Preferred acid-binding agents include sodium carbonate, potassium carbonate and sodium bicarbonate, and furthermore lower tertiary alkylamines, cycloalkylamines or arylalkylamines, for example triethylamine, N,N-dimethylbenzylamine and dicyclohexylamine, and furthermore pyridine and diazabicyclooctane.

The reaction temperatures can be varied within a substantial range in carrying out process variant (a). In general, the process is carried out at from 0° to 100° C., preferably from 10° to 80° C.

In carrying out process variant (a), 1 to 2 moles, or 0.5 mole in the case of a dimeric product, of carbamoyl chloride of the formula (III) and 1 to 2 moles of acid-binding agent are preferably employed per mole of the compound of the formula (II). Isolation of the compounds of the formula (I) is effected in a manner which is generally customary and known.

Preferred catalysts which can be used in process variant (b) are tertiary bases, such as triethylamine and pyridine, and organo-tin compounds, such as dibutyl-tin dilaurate.

The reaction temperatures can be varied within a substantial range in carrying out process variant (b). In general, the process is carried out at from 0° to 100° C., preferably from 20° to 85° C.

In carrying out process variant (b), 1 to 2 moles of isocyanate of the formula (IV) are generally employed per mole of the compound of the formula (II). To isolate the compounds of the formula (I), the solvent is distilled off and the residue is worked up by customary methods.

The reaction temperatures can be caried within a substantial range in carrying out process variant (c). In general, the process is carried out at from 0° to 100° C., preferably from 0° to 85° C.

In carrying out process variant (c), 1 to 1.5 moles of phosgene and 1 to 1.5 moles of amine of the formula (V) are preferably employed per mole of the compound of the formula (II). It has proved advantageous to employ the acid-binding agent in a slight excess (up to about 30 percent by weight) and, if appropriate, to employ the sodium hydride in an excess of up to about 50 percent by weight. Isolation of the compounds of the formula (I) is effected in the customary manner.

The reaction temperatures can be varied within a substantial range in carrying out process variant (d). In general, the process is carried out at from 0° to 100° C. preferably from 10° to 50° C.

In carrying out process variant (d), the starting substances are preferably employed in equimolar amounts. Isolation of the compounds of the formula (I) is effected by customary methods.

In some cases it is also possible to carry out the individual stages of the preparation of the precursors of the oximes of the formula (II), and the reaction of the latter to give the substances according to the invention, in a so-called "one-pot" reaction, without isolating the particular intermediate product.

The active compounds are well tolerated by plants, have a favorable level of toxicity to warm-blooded animals, and can be used for combating arthropod pests, especially insects or acarids, or nematode pests which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Bianiulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example Blatta orientalis, Periplaneta americana, Leucophaea maderae, Blattella germanica, Acheta domesticus, Gryllotalpa spp., Locusta migratoria migratorioidaz, Melanoplus differentialis and *Schistocerca gregaria;* from the order of the Dermaptera, for example *Forficula auricularia;* from the order of the Isoptera, for example *Reticulitermes spp.;* from the order of the Anoplura, for example *Phylloxera vastatrix, Pemphigus spp., Pediculus humanus corporis, Haematopinus spp.* and *Linognathus spp.;* from the order of the Mallophaga, for example *Trichodectes spp.* and *Damalinea spp.;* from the order of the Thysanoptera, for example *Hercinothrips femoralis* and *Thrips tabaci;* from the order of the Heteroptera, for example *Eurygaster spp., Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Acnidiella aurantii, Aspidiotus hederae, Pseudococcus spp.* and *Psylla spp.;* from the order of the Lepidoptera, for example *Pectinophora gossypiella, Bupalus piniarius, Cheimatobia brumata, Lithocolletis blancardeila, Hyponomeuta padella, Plutella maculipennis, Malacosoma neustria, Euproctis chrysorrhoea, Lymantria spp., Bucculatrix thurberiella, Phyllocnistis citrella, Agrotis spp., Euxoa spp., Feltia spp., Earias insulana, Heliothis spp., Laphygma exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Cacoecia podana, Capua reticulana, Choristoneura fumiferana, Clvsia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varivestis,* Atomaria spp., *Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp.,* Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., *Conoderus spp., Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., *Chrysomyia spp., Cuterebra spp.,* Gastrophilus spp., Hyppobosca spp., Stomoxys spp., Cestrus spp., Hypoderma spp., Tabanus spp., Tannia spp., *Bibio hortulanus, Oscinella frit, Phorbia spp., Pegomyia hyoscyami, Ceratitis capitata, Dacus oleae* and *Tipula paludosa;* from the order of the Siphonaptera, for example *Xenopsylla cheopis* and *Ceratophyllus spp.;* from the class of the Arachnida, for example *Scorpic maurus* and *Latrodectus mactans;* from the order of the Acarina, for example Acarus siro, Argas spp., Ornithodoros spp., *Dermanyssus gallinae, Eriophyes ribis, Phyllocoptruta oleivora, Boophilus spp.,* Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp. and Tetranychus spp..

The plant-parasitic nematodes include Pratylenchus spp., *Radopholus similis, Ditylenchus dipsaci,* Tylenchulus semipenetrans, Heterodera spp., Meloidogyne spp., Aphelenchoides spp., Longidorus spp., Xiphinema spp., and Trichodorus spp..

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The present invention also provides an arthropodicidal or nematicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects or acarids) or nematodes which comprises applying to the arthropods or nematodes, or to a habitat thereof, a compound of the present invention alone or in the form of a composition containing as active ingredient a compound of the present invention in admixture with a diluent or carrier.

The present invention also provides a method of freeing or protecting domesticated animals from parasitical insects or acarids which comprises applying to said animals a compound according to the present invention, in admixture with a diluent or carrier.

The present invention further provides crops protected from damage by arthropods or nematodes by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from parasitical insects or acarids by the application to said animals of a compound according to the present invention, in admixture with a diluent or carrier.

Preparation of the novel compounds is shown in the following illustrative examples:

EXAMPLE 1

(A)

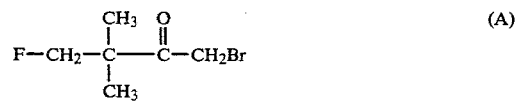

38 g (0.32 mol) of 3,3-dimethyl-4-fluoro-butan-2-one were dissolved in 250 ml of ether, and 52 g (0.325 mol)

of bromine were added dropwise at 20° C., while cooling. The mixture was subsequently stirred for 1 hour and the ethereal solution was washed five times with 100 ml of water each time, dried over sodium sulphate and concentrated in vacuo. The resulting 1-bromo-3,3-dimethyl-4-fluoro-butan-2-one was reacted further without additional purification.

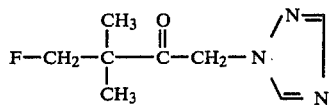

(B)

A solution of the 1-bromo-3,3-dimethyl-4-fluorobutan-2-one obtained in (A), in 50 ml of acetone, was added dropwise to a mixture of 23.1 g (0.33 mol) of 1,2,4-triazole and 46.2 g (0.4 mol) of potassium carbonate in 250 ml of acetone at room temperature, while cooling. The mixture was subsequently stirred at 20° C. for 4 hours, the inorganic precipitate was filtered off and the filtrate was concentrated in vacuo. The resulting oily 3,3-dimethyl-4-fluoro-1-(1,2,4-triazol-1-yl)-butan-2-one was reacted further without additional purification.

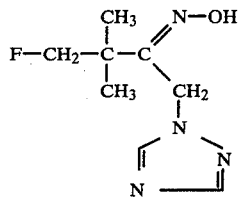

(C)

The 3,3-dimethyl-4-fluoro-1-(1,2,4-triazol-1-yl)-butan-2-one obtained in (B), 42 g (0.6 mol) of hydroxylamine hydrochloride and 33 g (0.33 mol) of triethylamine were dissolved in 250 ml of ethanol and the solution was heated under reflux for 5 hours. Thereafter, the solution was concentrated almost to dryness by distilling off the solvent. The residue was taken up in water and the resulting crystals were filtered off. 24 g (37.5% of theory, relative to the 3,3-dimethyl-4-fluoro-butan-2-one employed in (A) of 3,3-dimethyl-4-fluoro-2-oximino-1-(1,2,4-triazol-1-yl)-butane of melting point 124°–126° C. were obtained.

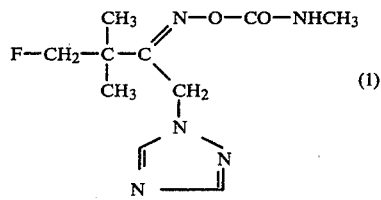

(D)

Process variant (b)

6 g (0.03 mol) of 3,3-dimethyl-4-fluoro-2-oximino-1-(1,2,4-triazol-1-yl)-butane were dissolved in 100 ml of methylene chloride, and 5 ml (0.06 mol) of methyl isocyanate were added, while stirring. The mixture was left to stand at room temperature for 12 hours and the volatile constituents were then distilled off in vacuo. The oily residue was brought to crystallization by trituration with petroleum ether. 7 g (90% of theory) of 3,3-dimethyl-4-fluoro-2-methylcarbamoyloximino-1-(1,2,4-triazol-1-yl)-butane of melting point 78°–79° C. were obtained.

EXAMPLE 2

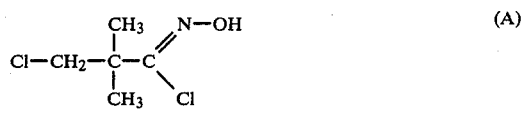

(A)

45 g (0.37 mol) of 3-chloro-2,2-dimethyl-propanol and 39 g (0.55 mol) of hydroxylamine hydrochloride were stirred into 200 ml of water, and a solution of 29 g (0.27 mol) of sodium carbonate in 100 ml of water was added dropwise. The reaction solution was stirred at room temperature for 5 hours and then adjusted to a pH value of 1 with 20 ml of concentrated hydrochloric acid. Thereafter, 30 g of chlorine were passed in at 0°–5° C. The lower organic phase was then separated off and the crude 1,3-dichloro-2,2-dimethyl-1-oximino-propane was directly reacted further.

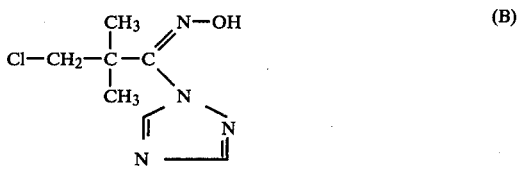

(B)

30.6 g (0.44 mol) of 1,2,4-triazole and 59 g (0.55 mol) of sodium carbonate were dissolved in 300 ml of water, and the crude 1,3-dichloro-2,2-dimethyl-1-oximino-propane obtained in (A) was then added dropwise at room temperature. The mixture was stirred at 20° C. for 5 hours and extracted several times with methylene chloride. The combined methylene chloride phases were dried over sodium sulphate and concentrated in vacuo. After trituration with diisopropyl ether, the residue crystallized. 13 g (17.5% of theory, relative to the 3-chloro-2,2-dimethylpropanol employed in the 1st stage) of 3-chloro-2,2-dimethyl-1-oximino-1-(1,2,4-triazol-1-yl)-propane of melting point 148°–153° C. were obtained.

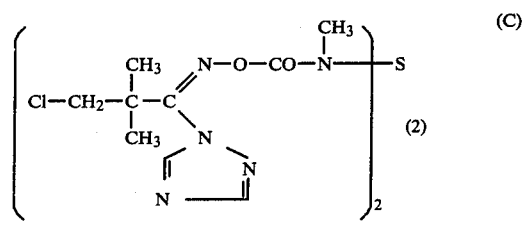

(C)

Process variant (a)

5 g (0.025 mol) of 3-chloro-2,2-dimethyl-1-oximino-1-(1,2,4-triazol-1-yl)-propane and 2.3 g (0.0125 mol) of thio-bis-(N-methyl-carbamic acid fluoride) were dissolved in 50 ml of dioxane, and 2.5 g (0.025 mol) of triethylamine were added dropwise at 20°–25° C. After the reaction mixture had stood at room temperature for 12 hours, 100 ml of water were added. The solid product which had separated out was filtered off, washed with water and dried. 5 g (73% of theory) of N,N'-bis-[3-chloro-2,2-dimethyl-1-oximinocarbonyl-1-(1,2,4-triazol-1-yl)-propane]-thio-bis-methylamine of melting point 168°–170° C. were obtained.

The following compounds in Table 2 were obtained analogously to Examples 1 and 2:

TABLE 2

$$X-\underset{\underset{Az}{\overset{|}{(CH_2)_n}}}{\overset{|}{C}}=N-O-CO-N\underset{R^2}{\overset{R^1}{\diagup}} \quad (I)$$

| Compound No. | X | Az | n | $R^1$ | $R^2$ | Melting point (°C.) |
|---|---|---|---|---|---|---|
| 3 | $Cl-CH_2-\underset{\underset{CH_3}{\overset{CH_3}{\vert}}}{\overset{\vert}{C}}-$ | $-N\underset{N=}{\diagdown}\overset{\diagup=N}{\diagup}$ | 1 | H | $CH_3$ | Oil |
| 4 | $CH_3-COO-CH_2-\underset{\underset{CH_3}{\overset{CH_3}{\vert}}}{\overset{\vert}{C}}-$ | $-N\underset{N=}{\diagdown}\overset{\diagup=N}{\diagup}$ | 1 | H | $CH_3$ | Oil |
| 5 | $\underset{\underset{CH_3}{\overset{CH_3}{\vert}}}{\overset{\overset{CH_3}{\vert}\phantom{xxx}}{\underset{COO-CH_2-C-}{\overset{NH}{\vert}}}}$ | $-N\underset{N=}{\diagdown}\overset{\diagup=N}{\diagup}$ | 1 | H | $CH_3$ | Crystal sludge |
| 6 | $HO-CH_2-\underset{\underset{CH_3}{\overset{CH_3}{\vert}}}{\overset{\vert}{C}}-$ | $-N\underset{N=}{\diagdown}\overset{\diagup=N}{\diagup}$ | 1 | H | $CH_3$ | 146–49 |
| 7 | $Cl-CH_2-\underset{\underset{CH_3}{\overset{CH_3}{\vert}}}{\overset{\vert}{C}}-$ | $-N\underset{N=}{\diagdown}\overset{\diagup=N}{\diagup}$ | 0 | H | $CH_3$ | 103–07 |
| 8 | $CH_3-COO-CH_2-\underset{\underset{CH_3}{\overset{CH_3}{\vert}}}{\overset{\vert}{C}}-$ | $-N\underset{N=}{\diagdown}\overset{\diagup=N}{\diagup}$ | 0 | H | $CH_3$ | Oil |
| 9 | $CH_3-COO-CH_2-\underset{\underset{CH_3}{\overset{CH_3}{\vert}}}{\overset{\vert}{C}}-$ | $-N\underset{N=}{\diagdown}\overset{\diagup=N}{\diagup}$ | 0 | $CH_3$ | dimer | Oil |
| 10 | $CH_3-\underset{\underset{CH_2F}{\overset{CH_2F}{\vert}}}{\overset{\vert}{C}}-$ | $-N\underset{N=}{\diagdown}\overset{\diagup=N}{\diagup}$ | 1 | H | $CH_3$ | 78–79 |

The insecticidal, acaricidal and nematocidal activity of the compounds of this invention is illustrated by the following examples wherein the compounds according to the present invention are each identified by the number (given in brackets) from the preparative examples hereinabove:

EXAMPLE 3

Doralis test (systemic action)

Solvent: 3 parts by weight of dimethylformamide

Emulsifier: 1 part by weight of alkylaryl polyglycol ether

To produce a suitable preparation of active compound, 1 part by weight of the active compound was mixed with the stated amount of solvent and the stated amount of emulsifier and the concentrate was diluted with water to the desired concentration.

Bean plants (*Vicia faba*) which had been heavily infested with the bean aphid (*Doralis fabae*) were each watered with 20 ml of the preparation of the active compound in such a way that the preparation of the active compound penetrated into the soil without wetting the leaves of the bean plants. The active compound was taken up from the soil by the bean plants and thus passed to the infested leaves.

After the specified periods of time, the destruction in % was determined. 100% meant that all the aphids had been killed; 0% meant that none of the aphids had been killed.

In this test, for example, the following compounds showed a superior action compared to the prior art: (7), (3) and (2).

EXAMPLE 4

Tetranychus test (resistant)
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were treated by being dipped into the preparation of the active compound of the desired concentration.

After the specified periods of time, the degree of destruction was determined as a percentage: 100% meant that all of the spider mites were killed whereas 0% meant that none of the spider mites were killed.

In this test, for example, the following compounds showed a superior activity compared to the prior art: (7) and (3).

EXAMPLE 5

Root-systemic action
Test insect: *Myzus persicae*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of active compound per unit volume of soil, which is given hereinafter in ppm (=mg/l), was decisive. The treated soil was filled into pots and these were planted with cabbage (*Brassica oleracea*). The active compound could in this way be taken up from the soil by the plant roots and be transported into the leaves.

To demonstrate the root-systemic effect, only the leaves were infested with the above-mentioned test insects after 7 days. After a further 2 days, the results were evaluated by counting or estimating the dead insects. The root-systemic action of the active compound was deduced from the destruction data. It was 100% when all of the test insects had been killed and 0% when just as many test insects were still alive as in the case of the untreated control.

In this test, for example, the following compounds showed a superior activity compared to the prior art: (3) and (7).

EXAMPLE 6

Root-systemic action
Test insect: *Phaedon cochleariae* larvae
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of active compound per unit volume of soil, which is given hereinafter in ppm (=mg/l), was decisive. The treated soil was filled into pots and these were planted with cabbage (*Brassica oleracea*). The active compound could in this way be taken up from the soil by the plant roots and be transported into the leaves.

To demonstrate the root-systemic effect, only the leaves were infested with the above-mentioned test insects after 7 days. After a further 2 days, the results were evaluated by counting or estimating the dead insects. The root-systemic action of the active compound was deduced from the destruction data. It was 100% when all of the test insects had been killed and 0% when just as many test insects were still alive as in the case of the untreated control.

In this test, for example, the following compounds showed a superior activity compared to the prior art: (3) and (7).

EXAMPLE 7

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The treated soil was filled into pots, lettuce was sown in and the pots were kept at a greenhouse temperature of 27 degrees C.

After 4 weeks, the lettuce roots were examined for infestation with nematodes (root galls), and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

In this test, for example, the following compounds showed a superior activity compared to the prior art: (3) and (7).

It will be appreciated that the instant specification and examples are set forth by way of illustration and not limitation, and that various modifications and changes may be made without departing from the spirit and scope of the present invention.

What is claimed is:

1. A substituted alkanyl-azolyl oxime-carbamate of the formula

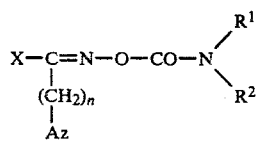

in which
- Az represents an imidazol-1-yl, 1,2,4-triazol-1-yl and 1,3,4-triazol-1-yl radical,
- $R^1$ represents hydrogen or alkyl with 1 to 4 carbon atoms;
- $R^2$ represents hydrogen, alkyl with 1 to 12 carbon atoms, alkenyl with 2 to 4 carbon atoms, alkynyl with 2 to 4 carbon atoms, halogenoalkyl with 2 to 4 carbon atoms and up to 5 halogen atoms or alkoxyalkyl with up to 2 carbon atoms in each alkyl part;
- n represents 0 or 1; and
- X represents monosubstituted or disubstituted alkyl with 1 to 4 carbon atoms, the substituents being selected from halogen, alkylcarbonyloxy with 1-4 carbon atoms in the alkyl part, carbamoyloxy, alkylcarbamoyloxy and dialkylcarbamoyloxy with in either case 1 to 4 carbon atoms in each alkyl part, alkylsulphonyloxy with 1 to 4 carbon atoms, hydroxyl, nitro, cyano, alkoxycarbonyl with 1 to 4 carbon atoms in the alkyl part and alkoxy and alkylthio with in either case 1 to 4 carbon atoms, or an acid addition salt or metal salt complex thereof.

2. A compound according to claim 1, in which X represents alkyl with 1 to 4 carbon atoms monosubstituted or di-substituted with halogen.

3. A compound according to claim 1, in which n is 1.

4. A compound according to claim 1, in the form of an acid-addition salt, the acid being selected from hydrogen halide acids, phosphoric acid, nitric acid, sulphuric acid, mono- and dicarboxylic and hydroxycarboxylic acids, and sulphonic acids.

5. A compound according to claim 1, in the form of a metal salt complex, the metal being selected from the metals of main groups II to IV and sub-groups I, II and IV to VIII of the Periodic Table and the anion being selected from the anions of hydrogen halide acids, sulphuric acids, nitric acid and phosphoric acids.

6. A compound according to claim 1, wherein such compound is 3,3-dimethyl-4-fluoro-2-methylcarbamoyloximino-1-(1,2,4-triazol-1-yl)-butane of the formula

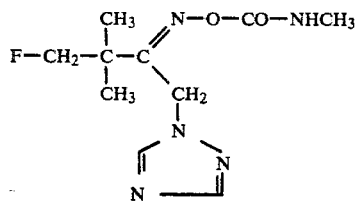

7. A compound according to claim 1, wherein such compound is 3,3-dimethyl-4-chloro-2-methylcarbamoyloximino-1-(1,2,4-triazol-1-yl)-butane of the formula

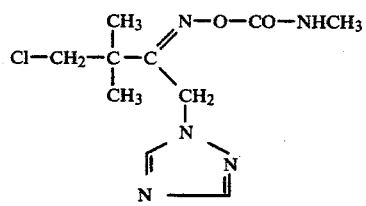

8. A compound according to claim 1, wherein such compound is 2,2-dimethyl-3-chloro-1-methylcarbamoyloximino-1-(1,2,4-triazol-1-yl)-propane of the formula

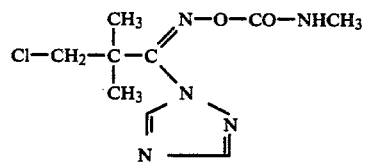

9. An arthropodicidal or nematocidal composition containing as active ingredient an arthropodicidally or nematocidally effective amount of a compound according to claim 1 in admixture with a diluent.

10. A method of combating arthropods or nematodes which comprises applying to the arthropods or nematodes, or to a habitat thereof, an arthropodicidally or nematocidally effective amount of a compound according to claim 1.

11. The method according to claim 10, wherein the compound is
3,3-dimethyl-4-fluoro-2-methylcarbamoyloximino-1-(1,2,4-triazol-1-yl)-butane,
3,3-dimethyl-4-chloro-2-methylcarbamoyloximino-1-(1,2,4-triazol-1-yl)-butane, or
2,2-dimethyl-3-chloro-1-methylcarbamoyloximino-1-(1,2,4-triazol-1-yl)-propane,
and it is applied to a domesticated animal thereby to free and protect said animal from parasitical insects.

* * * * *